United States Patent [19]

Parks

[11] Patent Number: 5,962,274
[45] Date of Patent: Oct. 5, 1999

[54] VIRAL VECTOR DIRECTED TO PREDETERMINED TARGET CELLS

[75] Inventor: Griffith D. Parks, Winston-Salem, N.C.

[73] Assignee: Wake Forest University, Winston Salem, N.C.

[21] Appl. No.: 09/041,987

[22] Filed: Mar. 13, 1998

[51] Int. Cl.$^6$ .............................. C12P 19/34; C07H 21/04
[52] U.S. Cl. .................. 435/91.1; 435/91.32; 435/91.33; 536/23.1; 536/23.4; 536/23.72; 536/24.1
[58] Field of Search ................................... 536/23.1, 24.1, 536/23.72, 23.4; 435/91.1, 91.32, 91.33

[56] References Cited

PUBLICATIONS

Matthias J. Schnell, et al, "Construction of a Novel Virus That Targets HIV–1–Infected Cells and Controls Cells and Controls HIV–1 Infection," Cell, vol. 90, Sep. 5, 1997, pp. 849–857.

Garry P. Nolan, "Harnessing Viral Devices as Pharmaceuticals: Fighting HIV–1's Fire with Fire," Cell, vol. 90, Sep. 5, 1997, pp. 821–824.

Murphy, S.K. and G.D. Parks, "Genome Nucleotide Lengths That Are Divisible By Six Are Not Essential But Enhance Replication Of Defective Interfering RNAs of The Paramyxovirus Simian Virus 5," Virology, vol., 1997, 232, pp. 145–157.

Sheshberadaran, H. et al, "Sequence Characterization of the Membrane Protein Gene of Paramyxovirus Simian Virus $5^1$,"Virology, vol. 176, 1990, pp. 234–243.

Thomas, et al, "Two mRNAs That Differ by Two Nontemplated Nucleotides Encode the Amino Coterminal Proteins P and V of the Paramyxovirus SV5," Cell, vol. 54, Sep. 9, 1988, pp. 891–902.

Zhou, et al, "Proper Spacing between Heptad Repeat B and the Transmembrane Domain Boundary Paramyxovirus SV5 F Protein Is Critical for Biological Activity," Virology, vol. 239, 1997, pp. 327–339.

Parks, et al. "Molecular cloning of the NP and L genes of simian virus 5: identification of highly conserved domains in paramyxovirus NP and L proteins," Virus Research, vol. 22, 1992, pp. 259–279.

Paterson, et al, "Analysis and Gene Assignment of mRNAs of a Paramyxovirus, Simian Virus 5," Virology, vol. 138, pp. 310–323, 1984.

Paterson, et al, "Expression at the cell surface of biologically active fusion and hemagglutinin/neuraminidase proteins of the paramyxovirus simian virus 5 from cloned cDNA," Proc. Natl. Acad. Sci. USA, vol. 82, pp. 7520–7524, Nov. 1985.

Chen, et al. "Potent antitumour activity of a new class of tumour–specific killer cells," Nature, vol. 385, pp. 78–80, Jan. 1997.

Choppin et al, "Phenotypic Mixing of Envelope Proteins of the Parainfluenza Virus SV5 and Vesicular Stomatitis Virus," Virology, vol. 5, May 1970, pp. 609–619.

Hiebert, et al, "Hemagglutinin–Neuraminidase Protein of the Paramyxovirus Simian Virus 5: Nucleotide Sequence of the mRNA Predicts an N–Terminal Membrane Anchor," Virology, vol. 54, Apr. 1985, pp. 1–6.

Horvath, et al, "Studies on the Fusion Peptide of a Paramyxovirus Fusion Glycoprotein: Roles of Conserved Residues in cell Fusion," Virology, vol. 66, Apr. 1992, pp. 2443–2455.

Lamb, Robert A., "Paramyxovirus Fusion: A Hypothesis for Changes," Virology, vol. 197, pp. 1–11, 1993.

Paterson, et al, "Fusion protein of the paramyxovirus simian virus 5: Nucleotide sequence of mRNA predicts a highly hydrophobic glycoprotein," Proc. Natl. Acad. Sci. USA, Nov. 1984, pp. 6706–6710.

Biao, et al, "Recovery of Infectious SV5 from Cloned DNA and Expression of a Foreign Gene," Virology, vol. 237, pp. 249–260, 1997.

*Primary Examiner*—Nancy Degen
*Attorney, Agent, or Firm*—Timothy S. Corder; Vinson & Elkins L.L.P.

[57] ABSTRACT

Disclosed are compositions comprising viral vectors derived from the paramyxovirus, simian virus 5 (SV5). The SV5 vectors of the present invention are designed so that the HN protein that binds to sialic acid is not expressed, and in certain embodiments a foreign membrane bound protein is expressed on the viral surface that targets the virus to particular cells or tissues. The vector then is able to deliver a toxin or cytotoxic agent to the target cell. Also disclosed are nucleic acid segments useful as viral genomes and methods of producing viral vectors.

38 Claims, 3 Drawing Sheets

HN PROTEIN
RECEPTOR BINDING

FUSION PROTEIN

CELL TYPE
SPECIFICITY

MOST CELLS

FIG. 1A

FUSION PROTEIN

CELL TYPE
SPECIFICITY

NO CELLS

FIG. 1B

FOREIGN MEMBRANE
PROTEIN

FUSION PROTEIN

CELL TYPE
SPECIFICITY

PREDETERMINED
CELL TYPES

```
        ←——— ANTIBODY ———→  ←——— F PROTEIN ———→
5'─┤                    ▨▨▨▨▨ ░░░░░░░ ├─3'
                        MEMBRANE  CYTOPLASMIC
                        SPANNING     TAIL
                        DOMAIN
```

FIG.3A

```
GENE START │ ANTIBODY-F │ GENE END
                 ↓
3'─┤ le │ NP │ P/V │ M │ F │SH│ HN │    L    │ tr ├─5'
```

FIG.3B

VIRAL VECTOR DIRECTED TO PREDETERMINED TARGET CELLS

BACKGROUND OF THE INVENTION

1. Field of the Invention

The invention is related to the fields of viral vectors for targeted gene therapy and pharmaceutical preparations, and more particularly to viral vectors for tumor therapy.

2. Description of the Related Art

The ability to deliver recombinant molecules to specific cells or tissues has been a long term goal of pharmaceutical therapeutics and gene therapy. Viruses and virus based vectors represent a powerful tool for these purposes, due to the efficiency of infection compared to other delivery systems and the high level of expression of recombinant molecules.

A distinct and widely recognized limitation of current virus-based delivery systems has been the lack of success in targeting these recombinant viruses to predetermined cell types or tissues. Thus, the enormous potential of viruses as delivery agents for pharmaceutical or gene therapy has been overshadowed by a technical roadblock, the inability of an infection by a recombinant virus to be specifically targeted and limited to a predetermined population of cells, a challenge termed "selective toxicity" (Nolan, 1997). There is a need, therefore, for a novel gene delivery system that provides a simple and flexible general method to overcome this limitation in controlling cell targeting by a recombinant virus.

BRIEF SUMMARY OF THE INVENTION

Figure 1A:
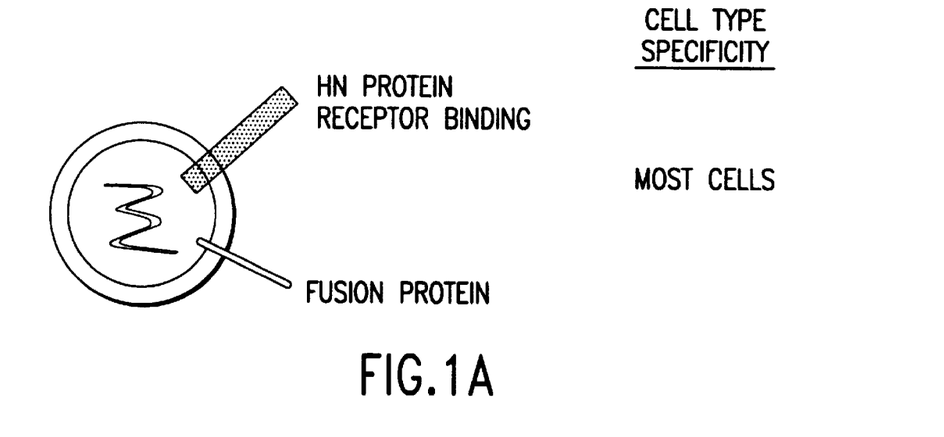
FIG. 1A. is a schematic representation of the structure of wild type SV5, with a native HN protein that functions as a receptor binding protein and an F protein or fusion protein. This virion has little cell type specificity. The concentric circles represent the virion lipid envelope and the squiggle represents the viral genome.

The present invention seeks to overcome this and other drawbacks in the prior art by providing a viral vector that can be targeted to a particular cell or cell type and can deliver a cytotoxic agent to the cell without the side effects or toxicities associated with other viral vectors. The viral vector system disclosed herein is based on properties of the viral glycoproteins that are unique to SV5. The lipid membrane of the paramyxovirus particle includes two viral integral membrane proteins (FIG. 1A). The hemagglutinin-neuraminidase (NH) functions in attachment to bind virions to sialic acid containing receptors on the host cell. Thus, wild type (WT) SV5 can attach to any cell that contains surface glycoproteins with sialic acid, which includes almost any cell type. After attachment, the fusion (F) protein is responsible for fusing the virion envelope with the cellular plasma membrane. For most paramyxoviruses, it is widely accepted that F-mediated fusion requires the homologous viral HN protein.

Figure 1B:
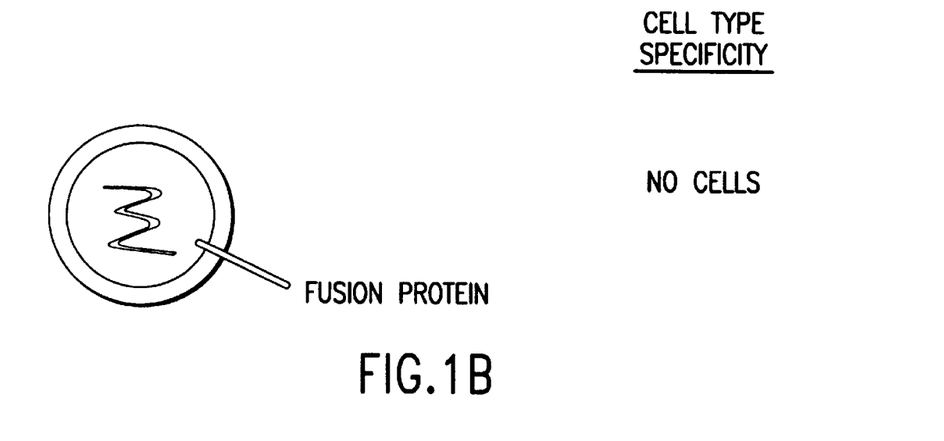
FIG. 1B. is a schematic representation of an SV5 that does not express HN ($HN_{minus}$). This virion does not have a cell recognition protein.
Figure 1C:
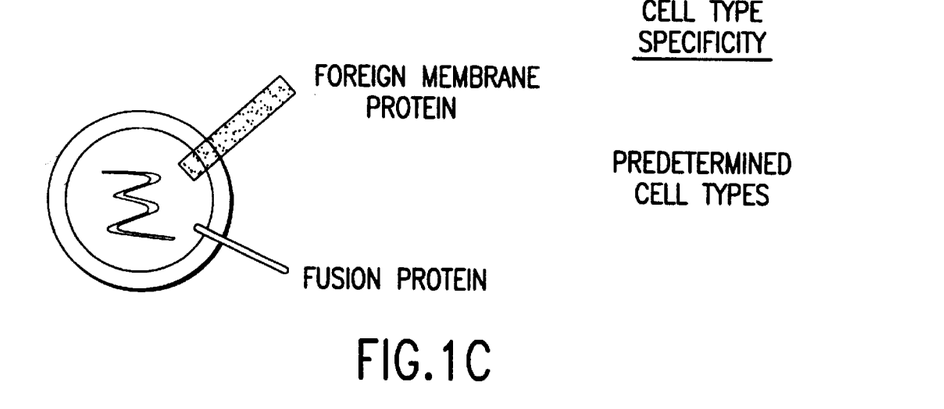
FIG. 1C. is a schematic representation of a recombinant SV5 expressing a foreign membrane protein and the native F protein. This virion has a predetermined host range restriction based on the recognition or binding ability of the foreign protein.

The SV5 F protein can cause efficient membrane fusion in the absence of the HN protein, a property that appears to be unique among the paramyxoviruses (Paterson et al., 1985; Horvath and Lamb, 1992). Therefore, a virus may be generated by deleting or inactivating the gene encoding the SV5 HN attachment protein, to create an HN minus virus (FIG. 1B). As an additional step, the present invention may then involve insertion into the SV5 genome of a foreign or exogenous gene encoding a membrane bound protein either in the position in the genome from which the HN encoding gene was deleted, or at another position within the genome (FIG. 1C). The foreign membrane bound protein is selected to be effective to target the virion to a particular cell type or tissue, such as a cancer cell, for example. The recombinant virions containing a foreign protein in the lipid envelope rather than the native HN protein are able to attach to and fuse via the F protein with target cells displaying the appropriate complementary surface molecule.

The toxins to be delivered by the vectors disclosed herein include agents that are cytotoxic or otherwise have anticellular activity, e.g. having the ability to kill or suppress the growth or cell division of cells. Exemplary anticellular agents include chemotherapeutic agents, radioisotopes, and cytotoxins. Examples of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or antitumor alkylating agents such as chlorambucil or melphalan. Also useful in the present invention are plant-, fungal- or bacterial-derived toxins, such as, by way of example, an A chain toxin such as ricin A, a ribosome inactivating protein, α-sarcin, aspergillin, restirictocin, a ribonuclease, ribozyme, diphtheria toxin or Pseudomonas exotoxin. Additional cytotoxic agents would include intracellular antibodies that block an essential cell process, leading to cell death, as described by Chen et al. (1994).

In certain embodiments, the present invention is a composition comprising a simian virus 5 viral vector having a lipid membrane and a genome including an HN gene region, wherein the viral vector does not express an integral membrane bound hemagglutinin-neuraminidase protein on the surface of the lipid membrane due to a mutation in the HN gene region. This embodiment would include any mutation that prevents the expression of the HN protein on the surface of the lipid membrane of the virus and includes any deletions in the coding region of the gene or even the deletion of the entire HN region including the gene start and end signals. It is also understood that such a deletion could be as small as one codon, the codon for the AUG translational start codon, for example, or even a single base deletion that results in the virion not being able to express the protein.

In certain embodiments, one may wish to delete at least a portion of the HN gene coding region, or alternatively one may wish to delete the entire coding region of the HN gene and leave the gene start and end sequences intact. In this way, one could insert a coding sequence for a foreign gene between these signals in order to express the foreign gene. As described herein one may delete the region from a Nael restriction site at the 5' end of the HN gene region to a Ndel restriction site at the 3' end of the HN gene region and insert a foreign gene into such a deletion. The sequence of the HN gene as used herein is described in Hiebert et al. (1985, incorporated in its entirety herein). In certain embodiments, one may also include an insertion in the viral genome that encodes a membrane bound protein having an extracellular portion that is effective to bind to a target molecule other than sialic acid. As described above, the native SV5 HN protein binds to any cell that has a sialic acid component on its surface, and certain vectors of the present invention are distinguished in that an extracellular target binding protein domain does not bind to sialic acid, but rather binds with a specific target molecule during use.

In certain embodiments the extracellular targeting domain is fused to the cytoplasmic and membrane spanning regions of the SV5 F protein. The regions include, based on the sequence of F protein as published in Paterson et al. (1984), the C terminal portion of the protein from the threonine encoded by bases 0.1443 to the C-terminal lysine on the end of the protein, or the amino acids encoded by bases 0.1443 to 0.1616 of SV5 F protein. The targeting protein may also comprise a portion of the extracellular region of SV5 F protein. This region may include from one to about 38 amino acids encoded by bases 0.1329 to 0.1442 of the extracellular region of SV5 F protein. It is understood that the fusion protein would include any amino acids from the F protein in the order in which they occur in the native protein. So that if one included one amino acid from the extracellular region, that would be the aspartate encoded by bases 0.1439–0.1442 and that any number of amino acids up to about 38 going in the C-terminal to N-terminal direction could be included.

In certain embodiments, the extracellular portion of the protein will comprise a single chain antibody domain fused to the F protein sequences as described in the previous paragraph. This single chain antibody domain may be selected to immunoreact during use with a tumor cell surface associated antigen. Immunoreact is defined herein to mean form an antibody/antigen binding pair as is understood in the art. The immunoreaction conditions would include binding in serum or physiologically relevant conditions such as found in an animal's circulatory system, or in a mammalian cell culture system. In certain embodiments, the tumor cell surface associated antigen is HER2, or it may be prostate specific membrane antigen. As described herein virtually any target molecule recognition domain may be used. Whenever an antibody is available that specifically targets a certain type of cell, and particularly a disease cell, such as a cancer cell, the vectors described herein can be targeted to that cell type using the antibody. These would include antibodies that recognize markers of any type of carcinoma, sarcoma, melanoma, or other cancer types for which markers are available. In addition, certain cancer cells are known to express increased levels of specific receptors such as a growth factor receptor, epidermal growth factor receptor for example. Therefore, targeting such receptors with an antibody or even a ligand would also be an aspect of the present invention. Other embodiments would include, but not be limited to expressing mutant versions of normal cellular proteins that are able to block or inhibit cellular processes, known as dominant negative mutations. Such mutations could be directed to intracellular steroid receptors, trimeric G proteins couples to adenyl cyclase, receptor tyrosine kinases such as receptors for platelet-derived growth factor, fibroblast growth factor, hepatocyte growth factor, insulin, insulin like growth factor, nerve growth factor, vascular endothelial growth factor or macrophage stimulating factors. To target neurons, one may use neuronal cell surface proteins such as acetylcholine receptor, glutamate receptor, or serotonin-gated cation channels.

It is also understood that the compositions, including the viral vectors described herein may comprise a pharmaceutically acceptable solution. Such a solution would be sterile and non-pyrogenic, suitable for injection, inhalation, or other route of administration to an animal or human subject.

An embodiment of the inventions of the present disclosure is a nucleic acid segment comprising an SV5 genome wherein the genome includes a deletion in the coding region of the HN gene such that the genome does not encode an SV5 membrane bound HN protein. Although the SV5 genome is an RNA molecule, included within the scope of the invention is also a DNA molecule comprising the full length complement of the RNA genome, or the full length complement of the DNA molecule. The complement of a nucleic acid sequence is well known in the art and is based on the anti-parallel, Watson-Crick pairing of nucleotides (bases) for a given nucleic acid polymer (strand). Two complementary strands of DNA are formed into a duplex by pairing of bases, e.g. "G" to "C", "C" to "G", "A" to "T" (in the case of DNA) or "U" (in the case of RNA) and all "T" or "U" to "A", in reverse 5' to 3' orientation (anti-parallel).

As used herein therefore, the term "complement" defines a second strand of nucleic acid which will hybridize to a first strand of nucleic acid to form a duplex molecule in which base pairs are matched as G:C, C:G, A:T/U or T/U:A. The full length complement simply means the complement of the full length.

A nucleic acid segment as described above may also comprise the coding sequence for a fusion of the cytosolic and membrane spanning regions of SV5 F protein and an extracellular cell targeting protein region and these regions may be inserted into the genome in the position of the deleted HN protein coding sequence. The extracellular cell targeting protein region may be a single chain Fv antibody, or a receptor ligand, and may be an antibody that binds to HER-2, or to prostate specific membrane antigen, for example. A nucleic acid segment as described herein may also comprise a coding sequence for a cytotoxic agent, wherein the cytotoxic agent is expressed from a gene start and gene end signal of SV5, and may also include an internal ribosome entry site operatively linked to the coding sequence for a cytotoxic agent. By operatively linked, is meant that the ribosome entry site is within the mRNA sequence for the gene and is effective to initiate ribosome binding to the transcript and subsequent translation of the mRNA into a polypeptide product. The cytotoxic agents may be any agent described herein and would include in certain embodiments a Pseudomonas exotoxin, or herpes simplex thymidine kinase.

An aspect of the present invention is also a method of making a viral vector comprising obtaining a plasmid containing a DNA copy of an SV5 genome; deleting the HN encoding gene from the DNA copy of the SV5 genome to obtain an HN deletion; inserting into the HN deletion, a nucleic acid segment including a coding sequence for a fusion of the SV5 F protein carboxy terminal and membrane spanning regions fused to a single chain Fv antibody transferring the plasmid into a cell; transferring into the cell helper plasmids that express viral replication proteins, NP, P and L in the cell; generating the correct 3' end of the DNA; and recovering the viral vector from the cell. This method may also include inserting into the genome a nucleic acid segment encoding a cytotoxic agent and SV5 gene start and end sequences effective to express the cytotoxic agent in a cell. The cells may express a T7 RNA polymerase and in that case the NP, P and L proteins are expressed from T7 RNA polymerase promoters, but any RNA promoter may be used.

An embodiment of the invention is also a method of killing a tumor cell that expresses a tumor cell specific surface antigen comprising providing an rSV5 vector that expresses a membrane bound antibody, immunoreactive during use with the tumor cell specific surface antigen and that also expresses a cytotoxic agent and contacting the tumor cell with the vector. In this method, the tumor cell specific surface antigen may be HER-2, or prostate specific membrane antigen, or any other tumor antigen as described herein. Various cytotoxic agents or toxins may be used in this method, including thymidine kinase, a Pseudomonas exotoxin such as exotoxin A, or an antisense RNA molecule.

Contacting a cell may occur ex vivo, as in a cell culture or a blood or tissue sample or it may occur in an animal, even a human. When such a cell is in an animal or human subject, the vector may be administered to the subject in a pharmaceutically acceptable solution. Administration may be by various methods as described herein.

BRIEF DESCRIPTION OF THE DRAWINGS

For a detailed description of a preferred embodiment of the invention, reference will now be made to the accompanying drawings wherein.

DETAILED DESCRIPTION OF THE PREFERRED EMBODIMENTS

Viruses and virus-based vectors represent a powerful tool for the delivery of recombinant molecules to cells. A major drawback to current systems has been the inability to target and limit an infection by a recombinant virus to predetermined cell types or tissue. As disclosed herein the recombinant SV5 vectors can target and limit an infection to a predetermined population of cells.

An embodiment of the present invention utilizes the paramyxovirus, simian virus 5 (SV5), a common and non-pathogenic RNA virus. SV5 contains two viral glycoproteins in its envelope: the HN protein which functions in attachment to host cell receptors, and the F protein which fuses the virion envelope with the target cell plasma membrane. SV5 is engineered to encode a foreign glycoprotein in place of the normal viral attachment protein HN. Virions containing the foreign membrane protein in the viral envelope are then tested for their cell-type specificity, which is limited to cells expressing the ligand that is complementary to the virion-associated foreign protein or glycoprotein. SV5 is preferred for this virus gene delivery system, because the SV5 F protein is the only known paramyxovirus fusion protein which has been shown to act independently of its homologous HN attachment protein.

In one embodiment of the present invention, the cell-type specificity of an SV5 infection is predetermined by incorporating the appropriate foreign membrane protein into the viral envelope. In an example of this invention, recombinant SV5 (rSV5) is engineered to incorporate a membrane-bound form of a single chain antibody (sFv) into its envelope. The specificity of infection by this rSV5 is thus limited to cells expressing the appropriate surface antigen that is recognized by this antibody. This aspect of the disclosed compositions and methods affords a high degree of flexibility in choice of cell types to be targeted by the SV5 vectors. An example of this embodiment is virions that contain in their envelope an sFv to HER2, a cell surface antigen that is overexpressed in a large number of carcinomas. For example, HER2 is a cell surface membrane protein which is overexpressed in very large percentage (~25%) of human lung, breast, ovary and stomach carcinomas and expression levels correlate with the aggressiveness of malignancy (Salmon et al., 1989).

The present invention has important implications for medical biotechnology and the use of RNA viruses for delivery of recombinant molecules to cells. This system represents a simple and flexible general method that has wide applications to the fields of pharmaceuticals and gene therapy. One application is in the field of cancer therapy. In light of the present disclosure, one can create "designer" recombinant SV5 viruses that express both a novel receptor protein for targeting the infection, and an intracellular toxin. These viruses are powerful tools for targeting and limiting an infection to kill cells that express specific tumor antigens on their surface. Other embodiments of the invention are contemplated to target other types of disease cells, including immune system cells that are involved in autoimmune diseases, for example. In this embodiment, the virion would express an antibody that recognizes and binds to immune cells, thus destroying overactive immune cells and alleviating an autoimmune reaction. For example, certain T-cell antigens are known to be involved in rheumatoid arthritis and in multiple sclerosis, and such cells would present useful targets for a viral vector.

SV5

There is a growing interest in the use of non-integrating RNA viruses as pharmaceutical or gene delivery systems (Nolan, 1997; Mebatsion et al., 1997; Schnell et al., 1997). Paramyxoviruses are a diverse group of enveloped RNA viruses that are among the most common organisms in acute respiratory tract and systemic infections. This family includes simian virus 5 (SV5), Sendai virus, measles virus, respiratory syncytial virus (RSV), and mumps virus. SV5 is a non-integrating virus whose genome consists of a single strand of negative-sense RNA that encodes seven tandemly-linked genes. The viral polymerase initiates transcription at the 3' end of the genome and produces mRNAs through multiple initiation-termination reactions at each internal cistron by a "stop-start" mechanism (Lamb and Kolakofsky, 1996). A key feature of these viruses is that they do not replicate through a DNA intermediate, but rather employ an RNA-dependent RNA polymerase for genome replication. Very recently, powerful "reverse genetics" approaches have been developed to engineer infectious RNA viruses that express foreign genes whereby recombinant SV5 expressing a foreign gene can be recovered from a cDNA clone (He et al., 1997, incorporated in its entirety herein by reference).

An aspect of the present invention is a viral gene delivery system based on SV5. The technology is based on properties of the viral glycoproteins that are unique to SV5. The lipid membrane of the paramyxovirus particle contains two viral integral membrane proteins (FIG. 1). The hemagglutinin-neuraminidase (HN) functions in attachment to bind virions to sialic acid-containing receptors on the host cell. Thus, WT SV5 can attach to any cell that contains surface glycoproteins with sialic acid, a ubiquitous carbohydrate. As used herein, the term ubiquitous has its normal meaning of "being present everywhere," or on virtually any cell type. As such, a viral vector that binds to sialic acid does not offer the specificity necessary for a good viral vector. After attachment, the fusion (F) protein is responsible for fusing the virion envelope with the cellular plasma membrane. For most paramyxoviruses, it is widely accepted that F-mediated fusion requires the homologous viral HN protein (reviewed in Lamb, 1993).

An important feature of the SV5 system relates to the finding that the SV5 F protein can cause efficient membrane fusion in the absence of the HN protein, a property that is apparently unique among paramyxoviruses (Paterson et al., 1985; Horvath and Lamb, 1992). Based on this property of the F protein, the strategy for directing the cell-type specificity of an SV5 infection involves two steps. First, the at least a portion of the gene encoding the SV5 HN attachment protein is deleted from the viral genome to create an HN minus virus. Second, a foreign gene encoding a membrane-bound protein that is specific for a cell surface molecule on a target cell is now inserted into the genome of the HN minus virus. The foreign gene may be inserted into the deletion, or into another position in the genome, and long as it does not disrupt any of the other genes (FIG. 1). The recombinant virions expressing a foreign protein in the lipid envelope in place of HN then are able to attach to and fuse (via F protein) with target cells displaying the appropriate complimentary surface molecule.

There are many advantages to using SV5 as a novel virus gene delivery system, including (1) the RNA genome is relatively small but appears to have little or no packaging constraints, (2) the paramyxovirus "beads-on-a-string" gene expression strategy provides the potential to engineer a recombinant virus to express multiple tandemly-linked foreign genes, (3) SV5 can replicate for extended periods in a wide variety of cell types without producing apparent cytopathic effects, 4) SV5 is capable of infecting humans, but is not associated with any pathogenic characteristic (i.e., disease) and the population has no preexisting immunity, and (5) SV5 is capable of incorporating heterologous cell-surface proteins into the lipid envelope. An important property as stated above is that the fusion activity of the SV5 F protein does not require HN protein, a property that is apparently unique to the SV5 protein (Lamb, 1994).

An aspect of the present invention then, is the ability to engineer "designer" recombinant viruses with specificity for virtually any predetermined tissue or cell type that can be distinguished by a surface marker, by incorporating the appropriate membrane protein into the HN minus viral genome. The development of this technology has widespread applications in diverse areas of the pharmaceutical and biotechnology-based fields. An important application is in cancer therapy. It is possible in light of the present disclosure to engineer SV5 to express and incorporate antibodies to tumor-specific cell surface antigens in the virion envelope and thereby limit the tropism of the virus delivery system to tumor cells.

SV5 Genome

Figure 3A:
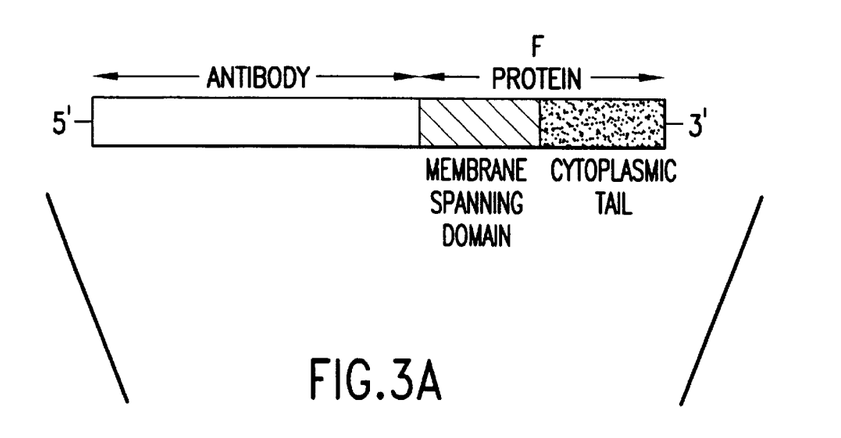
FIG. 3A. is a schematic representation of the structure of the chimeric sFv-F protein. The gene encoding the sFv-F protein chimera is shown schematically as a rectangle in the mRNA sense. The left portion represents the antibody domain, the hatched portion represents the membrane spanning domain derived from F protein, and the stippled portion represents the cytoplasmic tail of the F protein. The 5' and 3' denote viral gene start and gene end sequences.
Figure 3B:
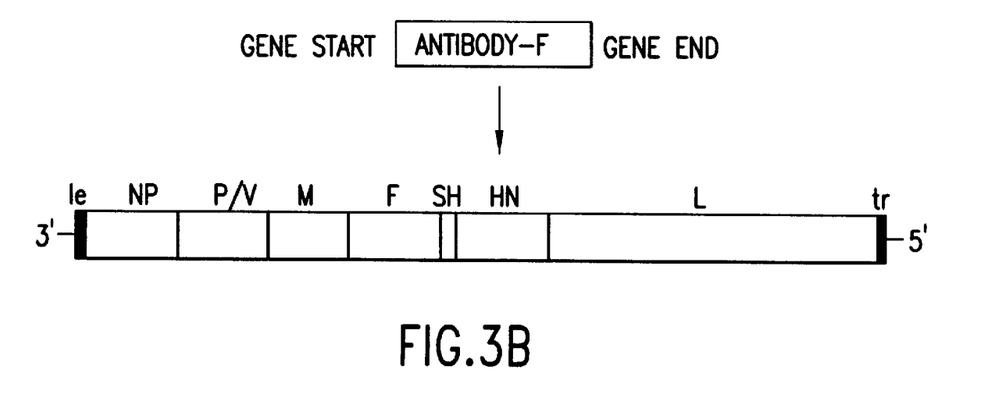
FIG. 3B. is a schematic representation of the structure of the SV5 genome. The SV5 genome is shown schematically as a rectangle with open boxes representing the seven tandemly-linked genes. Lines separating the genes denote the position of the gene start, intergenic and gene end sequences. le and tr are genomic RNA promoter elements. The sFv-F gene is substituted in place of the HN gene to create rSV5-sFv-F.

The SV5 genome is 15,246 nucleotides in length and exists in the virus as a single RNA (−) strand. The SV5 genome encodes in the 3' to 5' orientation, the nucleocapsid protein (NP), the V protein and P phosphoprotein, the matrix protein (M), the fusion protein (F), the small hydrophobic integral membrane protein (SH), the hemagglutinin-neuraminidase (HN), and the polymerase protein (L) (FIG. 3B).

cDNA clones of the SV5 genes have been reported including NP (Parks et al., 1992), V/P (Thomas et al., 1988), M (Sheshberadaran and Lamb, 1990), F (Paterson et al., 1984 a,b), HN (Hiebert et al., 1985), and L (Parks et al,. 1992) all incorporated herein by reference. A method of obtaining the entire genome based on the cDNA sequences is reported in He et al. (1997).

Antisense

In a practice of the present invention, one may use the SV5 vector to transfer an antisense transcript into a target cell. An antisense molecule, as used herein, indicates a molecule that is generally designed to inhibit the transcription, translation or both, of a given gene or construct and may also be used both in vitro and in vivo, for example, to inhibit gene expression in a given cell or host animal, including human cells and human subjects. For the purposes of this disclosure, antisense constructs are oligo- or polynucleotides comprising complementary nucleotides to the control regions or coding segments of a DNA molecule, such as a gene. Such constructs may include antisense versions of both the promoter and other control regions, exons, introns and exon:intron boundaries of a gene. Antisense molecules are designed to inhibit the transcription, translation or both, of a given gene or construct, such that the levels of the resultant protein product are reduced or diminished. Antisense RNA constructs, or DNA encoding such antisense RNAs, may be employed to inhibit gene transcription or translation or both within a host cell, either in vitro or in vivo, such as within a host animal, including a human subject.

Antisense embodiments of the invention would include, but not be limited to antisense molecules directed to proto-oncogenes such as c-myc, fos, jun, rel, abl, lck, neu (Bishop et al, 1985), or they could be directed to pro-inflammatory mediators or cytokines. Examples include interleukin-1 (IL-1), IL-2, IL-3, IL-4, IL-5, or tumor necrosis factor. Also included would be cell cycle cyclins such as Cdk2 and Cdc2 to inhibit the cell cycle.

Pharmaceutical Compositions

Aqueous compositions of the present invention comprise an effective amount of the SV5 viral vector, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

Aqueous carriers include water, alcoholic/aqueous solutions, saline solutions, parenteral vehicles such as sodium chloride, Ringer's dextrose, etc. Intravenous vehicles may include fluid and nutrient replenishers. Preservatives include antimicrobial agents, anti-oxidants, chelating agents and inert gases. The pH and exact concentration of the various components the pharmaceutical composition are adjusted according to well known parameters.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia, or other dermal hyperproliferative disorder. Alteratively, administration will be by orthotopic, intradermal subcutaneous, intramuscular, intraperitoneal or intravenous injection. Such compositions would normally be administered as pharmaceutically acceptable compositions that include physiologically acceptable carriers, buffers, or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient the route of administration, the intended goal of treatment (alleviation of symptoms versus cure) and the potency, stability and toxicity of the particular therapeutic substance.

The following examples are offered by way of illustration and are not intended to limit the scope of the invention in any manner. All of the materials used in these examples were obtained from well known commercial sources, or as specifically stated in the examples. Essentially conventional methods were employed in each instance where no specific procedure is stated.

EXAMPLE 1

Figure 2:
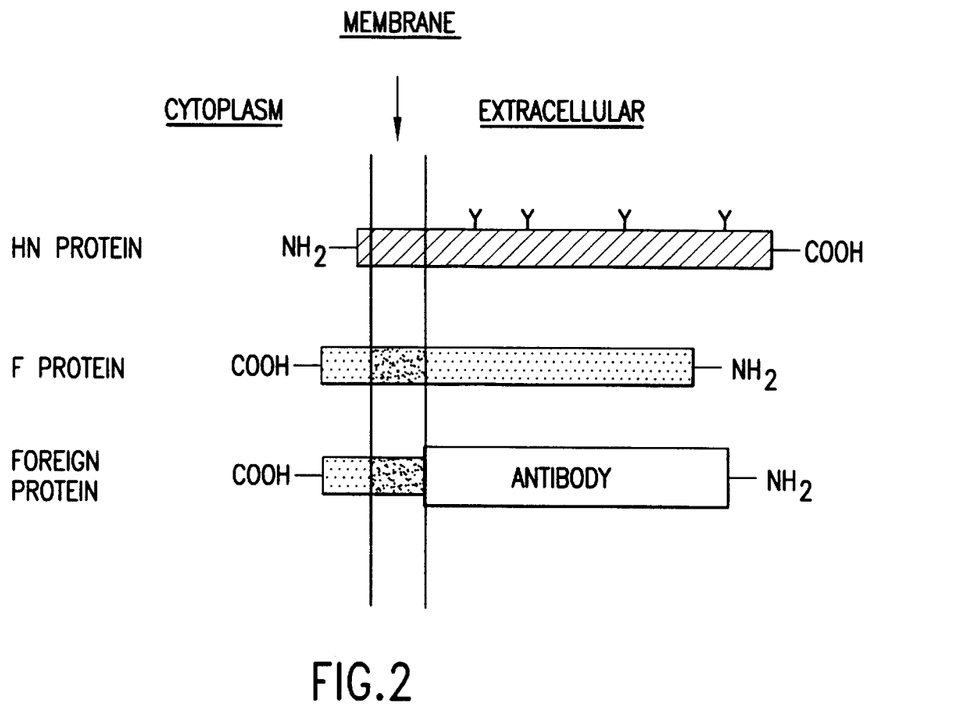
FIG. 2. is a schematic representation of the structure of viral membrane proteins and sFv-F protein chimera. The plasma membrane is depicted as two vertical lines with the cytoplasmic region on the left and the extra cellular region on the right. The top protein, represented by a hatched horizontal rectangle, is the HN protein. In all proteins, the amino and carboxy terminals are indicated. The Y structures indicate carbohydrate moieties of the glycoprotein. The middle protein, F, is indicated by the stippled rectangle. The lower protein is a representation of an embodiment of the invention in which an antibody domain is fused to the membrane and cytoplasmic regions of F protein. In certain embodiments, a portion of the F extracellular region is also present in the fusion.

The following example describes the construction of a chimeric F protein and sFv fusion. The erbB2 gene product HER2 is a cell surface marker that is overexpressed in a large number of carcinomas (Slamon et al., 1989). For the purposes of this example, one may utilize a mouse single chain antibody e23 which binds with high affinity to an extracellular domain on HER2, which is overexpressed on a variety of human carcinomas (Batra et al., 1992). A cDNA encoding this functional sFv is available as described in Chen et al. (1997). A membrane-bound form of the sFv polypeptide is generated such that the antigen binding region of the sFv is fused to the SV5 F protein membrane spanning domain and cytoplasmic tail (FIG. 2). The rationale behind using a chimera between the SV5 F protein and sFv is that both polypeptides have a type I orientation with an extracellular N-terminal domain, and this positions the antigen binding sites of the sFv on the outside of the plasma membrane (see FIG. 2). During the budding process, it is expected that the cytoplasmic tails of the viral HN and F proteins provide signals which promote incorporation into SV5 virions. Thus, including the F protein membrane spanning and cytoplasmic tail on the sFv-F serves the dual function of anchoring the chimera with the proper membrane topology and also promoting incorporation of the hybrid molecule into virions.

Using cDNAs which encode the functional anti-HER2 sFv (Batra et al., 1992; Chen et al. 1997) and the SV5 F protein (Paterson et al., 1984), two chimeric genes are constructed such that the extracellular antigen binding sites of the sFv are linked precisely to portions of the SV5 F protein (FIG. 3A). Briefly, the HER2-specific sFv consists of the variable region of the light chain of monoclonal antibody e23 attached through a short linker segment to the variable region of the heavy chain (Batra et al., 1992). This polypeptide has been shown to bind with very high affinity to cell surface HER2. Using PCR®-based methods (Parks, 1994), the sFv-F1 hybrid gene is constructed such that the sFv polypeptide is linked precisely with the F protein membrane spanning and cytoplasmic domains (FIG. 3A). For the purposes of this example, two hybrid genes are constructed, sFv-F1 and sFv-F2. The sFv-F2 hybrid gene differs from sFv-F1 by containing an additional polypeptide segment from the F protein extracellular domain. In turn, these two DNA fragments are engineered such that the final cDNA is flanked by the SV5 HN gene start and gene end sequences (Parks et al., 1992).

It is widely accepted that the position of a gene within the paramyxovirus genome is a major factor determining the level of gene expression, with those genes located furthest from the 3' le end of the promoter (e.g., HN and L) (FIG. 3B) being transcribed less than those located in a 3' proximal position (reviewed in Lamb and Kolakofsky, 1996). Thus, the level of sFv-F chimera expression from the rSV5 should match that of HN in the WT SV5 infection. In the event that there is an unacceptably low level of sFv-F expression, two modifications may be made to the sFv-F gene. One modification is to replace the HN gene end and gene start sequences flanking the sFv-F gene by those from the NP gene, because these are the most active of the SV5 transcription signals (Parks et al., 1992). Another modification is to engineer the 5' untranslated region of the sFv-F gene to include an internal ribosome entry site or "ribosome landing pad" (Parks et al., 1986) to enhance translation of the sFv-F message.

The basis for a system in which infectious SV5 can be recovered from a cDNA has been established (He et al., 1997; Murphy and Parks, 1997), thereby allowing one to do standard DNA manipulations such as restriction enzyme digestion, ligation, site directed mutagenesis, etc. and then recover an active RNA virus genome. As shown in FIG. 3B, the gene encoding the HN protein is deleted from the SV5 full-length cDNA clone pSV5 (He et al., 1997), by using the unique 5' end NaeI and 3' end NdeI restriction sites, thus forming the backbone for constructing the rSV5 viruses. The gene start-sFv-F-gene end cassettes described above are inserted into the NaeI/NdeI sites of the pSV5 backbone to generate two full length SV5-sFv-F genomes. As a control, one may construct a gene such that the sFv translational start codon is changed to a stop codon so that no protein can be translated from the gene. As is well known in the art, one could also delete the entire coding sequence of the HN gene or one could delete as little as the single triplet AUG that acts as the start codon for translation of the gene. Any such deletions that would abrogate expression of an HN protein would be useful in the practice of this embodiment. In addition, one of skill in the art could easily insert a polycloning region containing multiple restriction enzyme sites to use for insertion of foreign genes.

rSV5 is generated using established transfection procedures as described in Murphy and Parks (1997) as modified by He et al. (1997). Briefly, A549 human lung cells are infected with a replication defective recombinant vaccinia virus (MVA) which expresses T7 RNA polymerase. These infected cells are then cotransfected with a series of cDNA plasmids encoding the SV5 genome and SV5 polymerase proteins, each of which is under control of the T7 promoter. As previously documented (He et al. 1997; Murphy and Parks, 1997), proteins produced by T7 RNA polymerase from the transfected plasmids direct the replication of the SV5 genome and produce progeny SV5 virions. This procedure is well established in the field of negative strand viruses (Schnell et al., 1996; 1997). Thus, the three rSV5 viruses to be generated from cDNAs are rSV5-sFv-F1 and rSV5-sFv-F2 in which the two versions of the HER2 sFv-F chimera replace HN, and the control rSV5-sFv-stop virus in which the sFv gene cannot produce protein.

Because the rSV5 viruses lack the HN gene, plaque assays on typical cell lines are not feasible. To circumvent this, a plasmid encoding the HN protein (Parks and Lamb, 1990a) is included in the initial transfection during the generation of rSV5. The rationale is that the HN protein supplied in trans complements the HN minus viral genome, and allows an amplification from the initial transfection. However, the HN plasmid is not supplied in trans for subsequent studies when the amplified stock of rSV5-sFv-F is analyzed. As a possible alternative approach, one may, using standard molecular biology techniques, produce stable cell lines which express HN under control of the tet-inducible promoter. Thus, this cell line approach can be used as an alternative means to amplify rSV5 genomes which lack an HN gene.

The rSV5 viruses that have previously been amplified by HN complementation are analyzed by conventional methods (Parks et al., 1993; Murphy and Parks, 1997) to determine the viral growth characteristics. This includes: (a) Northern blotting of sFv-specific and viral mRNA, and (b) Western blotting of sFv and viral proteins. Because the sFv-F gene is placed in the equivalent position in the viral genome normally occupied by HN, this does not disrupt normal viral transcription of the other genes. While unlikely, infected cells may show differences in the synthesis of viral proteins, and this may be due to the presence of the sFv-F protein or to the new foreign transcription unit. Should such a problem arise, viral transcription signals from genes other than HN may be employed for this recombinant system.

In order to determine if the sFv-F protein encoded in the rSV5-sFv-F genome is incorporated into the envelope of progeny virions, cells are infected with WT SV5, rSV5-sFv-F1 or rSV5sFv-stop. Infected cells are radiolabeled from 10 to 18 hpi with [$^{35}$S]-amino acids. Extracellular virions produced during this labeling period are sedimented on 15–60% sucrose gradients (Parks and Lamb, 1990b) and fractions from the gradients are collected. Samples from each fraction are immunoprecipitated with antibodies to mouse IgG (Pharmingen, Inc) or to the viral nucleocapsid-associated proteins NP, P, and M before analysis by SDS-PAGE and autoradiography. The sFv-F chimera is expected to be detected as an MWr-75 kDa protein in the case of rSV5-sFv-F samples (Chen et al., 1997), but not in the case of the WT or rSV5-sFv-stop viruses. The most important aspect of this gradient analysis is to determine if the sFv-F cosediments to the same position in the gradient as the other viral polypeptides NP, P and M. To confirm that cosedimentation of sFv-F with these viral proteins is due to the presence of sFv-F in the virion envelope, detergent-disrupted rSV5-sFv-F virions are analyzed in a parallel gradient. In this case, it is expected that sFv-F sediments at the top of the gradient, a position distinct from that of the viral nucleocapsid-associated proteins.

In those embodiments in which the hybrid molecule that contains a foreign protein region linked to the F protein membrane spanning and cytoplasmic domains is not efficiently incorporated into virions the rSV5 that includes some extracellular portion of F (such as sFv-F2) may be used. For example, one may include in addition to the 58 amino acid that are the cytoplasmic and membrane spanning regions, any number of amino acids up to 36 additional amino acids that are contiguous with the membrane spanning domain in the native protein. This is an unlikely outcome, since infectious SV5 virions can readily incorporate foreign glycoproteins into the virion envelope to yield "pseudotypes" (Choppin, and Compans, 1970). However, this may be necessary in some cases because an extracellular heptad repeat sequence near the F protein transmembrane domain is a factor for F protein cell surface expression (Zhou et al., 1997). Thus, using various combinations of cytoplasmic tail and membrane spanning domains from F protein or other viral glycoproteins (e.g., Parks and Lamb, 1990a) one may enhance cell surface expression and incorporation of a fusion of F and a variety of foreign proteins into rSV5 virions.

EXAMPLE 2

The following example is a description of the use of recombinant SV5 (rSV5) as a targeted vector to direct infection specifically to HER2 positive cells. In the following studies, two human carcinoma cell lines are employed which express dramatically different levels of HER2. N87 cells are a human gastric carcinoma cell line which overexpresses cell surface HER2, and the anti-HER2 sFv shows very strong binding to these cells (Batra et al., 1992). A characteristic of the N87 cells which is important for preliminary studies is that they can be used to evaluate human tumor growth in a nude mouse model (Chen et al., 1997). The human mammary tumor cell line MCF expresses very low to undetectable levels of HER2, and the anti-HER2 sFv shows only background low level of binding to these cells (Chen et al., 1997). This cell line is predicted to be resistant to infection by rSV5-sFv-F. Other HER2-positive and -negative cell lines are also available (e.g., SKOV3, NIH/3T3).

rSV5 stocks are generated in the absence of HN complementation so that virions do not contain HN in their envelopes. Cell monolayers (~$10^5$ cells) are individually infected with one of three viruses: WT SV5, the rSV5-sFv-F virus or the rSV5-sFv-stop virus. After 18 hours, cells are analyzed for surface expression of the SV5 F protein by incubating with anti-F antibody (Paterson et al., 1989) followed by phycoerythrin-labeled secondary antibody. Flow cytometry analysis is performed (Alexander-Miller et al., 1996) to determine the percentage of the cells in the population that show staining for the viral F protein and the expression level. Cell surface staining for F protein indicates that the cells have been infected and are expressing viral proteins from the replicating viral genome. A549 human lung cells are fully permissive to WT SV5 and are used as a positive control for F cell surface staining (Parks and Lamb, 1990a). Table I lists the predicted outcomes.

TABLE 1

Predicted specificity of infection for the WT and recombinant SV5 viruses

|  | N87 cells | MCF cells | A549 cells |
|---|---|---|---|
| WT SV5 | + | + | + |
| rSV5-sFv-stop | − | − | − |
| LrSV5-sFv-F | + | − | − |

It is expected that the positive control WT SV5 infects both the N87 and MCF cell lines in this assay, because the normal receptor for the virus is the ubiquitous cell surface carbohydrate sialic acid. rSV5-sFv-stop lacks a virion-associated receptor protein, and it is expected that this negative control virus is not infectious to any cell types. The most important sample is the rSV5-sFv-F infected cells. It is expected that rSV5-sFv-F infects and replicates in the N87 cells but not in the MCF cells. Thus, the virion-associated sFv-F binds specifically to the HER2 molecules on N87 cells, while the HER2-negative MCF cells are not infected. This result is evidenced by detection of cell surface staining in the case of N87 cells, and no F protein-specific staining in the case of MCF cells. Western blotting of cell lysates using antibodies to viral proteins (e.g., NP, P, L) and anti-mouse IgG serum (to detect the sFv polypeptide) are carried out to verify the results from the above cytometric analysis.

A virus neutralization study is carried out to confirm that the virion-associated sFv-F is directing the tropism of the infection. WT SV5 or rSV5-sFv-F virus are preincubated with antiserum specific for mouse IgG, or negative control serum or antiserum specific for the SV5 F protein (Randall et al., 1987). The ability of these treated virus samples to initiate an infection of N87 cells is assayed by Western blotting of cell lysates using an antiserum to the viral NP protein. It is expected that preincubation with the anti-F serum neutralizes the infectivity of both viruses and that preincubation with the negative control serum has no effect on infectivity.

In addition to engineering the rSV5 for specific targeting, the necessary gene to kill predetermined target tumor cells is added. In the practice of this embodiment, one may engineer SV5 to encode the appropriate sFv to the target cell surface, but also to encode a toxin (e.g., Pseudomonas toxin), antisense RNA, or some other specific cellular enzyme (Chen et al., 1996). A toxin that may be used is the herpes virus thymidine kinase (TK) protein that would be selectively toxic to rSV5-infected cells, but only when acyclovir is administered. As described herein and elsewhere, the paramyxovirus "beads-on-a-string" coding strategy is ideal for the delivery of these multiple foreign genes from a single recombinant virus. Because the SV5 genome does not appear to be limited to a particular size, other than a preference for a genome length that is a multiple of 6 (Murphy and Parks, 1997) there is not a limit to the size of toxin gene that can be added to the SV5 genome. As described above, the gene start and end signals from virtually any of the SV5 genes may be used to express a foreign toxin or cytotoxic protein. These may preferably be the HN signals, but signals from other SV5 genes may also be effective. In the practice of the invention, it may also be advantageous to place the foreign genes upstream of the L gene, in order to facilitate replication. However, as discussed above, translation of any foreign gene may be facilitated by the addition of an internal ribosome binding site.

Alternate embodiments of the present example would include, but not be limited to other types of cancer cell-specific antigens. An increasing number of tumor-specific antigens are being identified, such as the 5T4 oncofetal trophoblast antigen, for example (Myers et al., 1994) whose expression is strongly linked to colonorectal and gastric cancer cells. In addition, there are receptors for hormones and growth factors such as epidermal growth factor receptor that are preferentially expressed on certain types of tumor cells. The use of the present invention is contemplated for use in targeting virtually any cell surface molecule for which there is specific mAb or ligand available. Another example is prostate cancer cells. Prostate-specific membrane antigen (PSMA) is a recently described prostate biomarker that is overexpressed in metastatic prostate carcinomas (Troyer et al., 1997) and would be useful in targeting a rSV5 vector to prostate cancer cells.

While the preferred embodiment of the invention has been shown and described, modifications thereof can be made by one skilled in the art without departing from the spirit and teachings of the inventions. The embodiments described herein are exemplary only, and not limiting. Many variations and modifications of the compositions and methods disclosed herein are possible and are within the scope of the inventions. Accordingly, the scope of protection is not limited by the description set out above, but is only limited by the claims which follow, that scope including all equivalents of the subject matter of the claims.

REFERENCES

All patents and publications referred to in this application are incorporated herein by reference to the same extent as if each was specifically indicated as being incorporated by reference and to the extent that they provide materials and methods not specifically shown.

Alexander-Miller, M. A., G. R. Leggatt, A. Sarin, and J. A. Berzofsky. 1996. Role of antigen, CD8, and CTL avidity in apoptosis of effector CTL. J. Exp. Med. 184:485–492.

Batra, J. K., P. G. Kasprzyk, R. E. Bird, 1. R. Pastan, and C. R. King. 1992. Recombinant antierbB2 immunotoxins containing Pseudomonas exotoxin. Natl. Acad. Sci. USA. 89:58675871.

Chen, S.-Y., A.-G. Yang, J.-D. Chen, T. Kute, C. r. King, J. Collier, Y. Cong, C. Yao, and X. F. Huang. 1997. Potent antitumor activity of a new class of tumour-specific killer cells. Nature 385: 78–80.

Chen, S.-Y., and W. A. Marasco. 1996. Novel genetic immunotoxins and intracellular antibodies for cancer therapy. Seminars in Oncology. 23:148–53

Chen, S. Y., J. Bagley and W. A. Marasco, 1994. Human Gene Therapy 5:595–601.

Choppin, P. W., and R. W. Compans. 1970. Phenotypic mixing of enveloped proteins of the parainfluenza virus SV5 and vesicular stomatitis virus. J. Virol. 5:609–616.

Cramer, S. D., D. M. Peehl, M. G. Edgar, S. T. Wong, L. J. Deftos and D. Feldman. 1996. Parathyroid hormone-related protein (PTHrP) is an epidermal growth factor-regulated secretory product of human prostatic epithelial cells. Prostate 29:20–9.

He, B., R. G. Paterson, C. D. Ward and R. A. Lamb. 1997. Recovery of infectious SV5 from cloned DNA and expression of a foreign gene. Virology 237:249–260.

Hiebert, S. W., Paterson, R. G., and Lamb, R. A., 1985, J. Virol. 54:1–6.

Horvath, C. M., and R. A. Lamb. 1992. Studies on the fusion peptide of a paramyxovirus fusion glycoprotein: roles of conserved residues in cell fusion. J. Virol. 66:2443–2455.

Lamb, R. A. 1993. Paramyxovirus fusion: a hypothesis for changes. Virology 197: 1–11.

Lamb, R. A., and D. Kolakofsky. 1996. Paramyxoviridae: the viruses and their replication. In B. N. Fields, D. M. Knipe and P. M. Howley (Eds), Virology, 3rd edition, Lippincott-Raven, New York, pp 1177–1204.

Mebatsion, T., S. Finke, F. Weiland, and K.-K. Conzelmann. 1997. A CXCR4/CD4 pseudotype rhabdovirus that selectively infects HIV-1 envelope protein-expressing cells. Cell 90:841–847.

Murphy, S. K. and G. D. Parks. 1997. Genome nucleotide lengths that are divisible by six are not essential but enhance replication of defective interfering RNAs of the paramyxovirus simian virus 5. Virology 232:145–157.

Myers, K. A., V. Rahi-Saund, M. D. Davison, J. A. Young, A. J. Cheater, and P. L. Stem. 1994. Isolation of a cDNA encoding 5T4 oncofetal trophoblast glycoprotein. J. Biol. Chem. 269:9319–9324.

Nolan, G. P. 1997. Harnessing viral devices as pharmaceuticals: fighting HIV-1's fire with fire. Cell 90:821–824.

Parks, G. D. 1994. Mapping of a region of the paramyxovirus L protein required for the formation of a stable complex with the viral phosphoprotein P. J. Virol. 68:4862–4872.

Parks, G. D., G. M. Duke, and A. C. Palmenberg. 1986. Encephalomyocarditis virus 3C protease: efficient cell-free expression from clones which link viral 5' noncoding sequences to the P3 region. J. Virol. 60:376–384.

Parks, G. D., and R. A. Lamb. 1990a. Defective assembly and intracellular transport of mutant paramyxovirus hemagglutinin-neuraminidase proteins containing altered cytoplasmic domains. J. Virol. 64:3605–3616.

Parks, G. D., and R. A. Lamb. 1990b. Folding and oligomerization properties of a soluble and secreted form of the paramyxovirus heamagglutinin-neuraminidase glycoprotein. Virology 178:498–508.

Parks, G. D., and R. A. Lamb. 1991. Topology of eukaryotic type 11 membrane proteins: Importance of N-terminal positively charged residues flanking the hydrophobic domain. Cell 64:777–787.

Parks, G. D., C. D. Ward, and R. A. Lamb. 1992. Molecular cloning of the NP and L genes of simian virus 5: Identification of highly conserved domains in paramyxovirus NP and L proteins. Virus Research 22, 259–279.

Parks, G. D., and R. A. Lamb. 1993. Role of NH2-terminal positively charged residues in establishing membrane protein topology. J. Biol. Chem. 268:19101–19109.

Paterson, R. G., Harris, T. J. R., and R. A. Lamb, 1984a, Virology 138:310–323.

Paterson, R. G., Harris, T. J. R., and R. A. Lamb, 1984b, Proc. Natl. Acad. Sci. USA. 81:6706–6710.

Paterson, R. G., S. W. Hiebert and R. A. Lamb. 1985. Expression at the cell surface of biologically active fusion and hemagglutinin/neuraminidase proteins of the paramyxovirus simian virus 5. Proc. Natl. Acad. Sci. USA. 82:7520–7524.

Peluso, R. W., R. A. Lamb, and P. W. Choppin. 1977. Polypeptide synthesis in simian virus 5 infected cells. Virology 23:177–187.

Randall, R. E., D. F. Young, K. K. A. Goswami, and W. C. Russell. 1987. Isolation and characterization of monoclonal antibodies to simian virus 5 and their use in revealing antigenic differences between human, canine and simian isolates. J. Gen. Virol. 68: 2769–2780.

Slamon, D. J., W. Godophi, L. A. Jones, J. A. Holt, S. G. Wong, D. E. Keith, W. J. Levine, S. G. Stuart, J. Udove, A. Ulrich and M. F. Press. 1989. Studies of the HER-2/neu proto-oncogene in human breast and ovarian cancer. Science 244:707–712.

Schnell, M. J., J. E. Johnson, L. Buonocore, and J. K. Rose. 1997. Construction of a novel virus that targets HIV-1-infected cells and controls HIV-1 infection. Cell 90:849–857.

Schnell M. J., L. Buonocore, E. Kretzschmar, E. Johnson and J. K. Rose. 1996. Foreign glycoproteins expressed from recombinant vesicular stomatitis viruses are incorporated efficiently into virus particles. Proc. Natl. Acad. Sci. USA 93:11359–65.

Sheshberadaran, H., and Lamb, R. A., 1990. Virology 176:234–243.

Thomas, S. M. Lamb, R. A., and Paterson, R. G. 1988. Cell 54:891–902.

Troyer J. K., M. L. Beckett and G. L. Wright. 1997. Location of prostate-specific membrane antigen in the LNCaP prostate carcinoma cell line. Prostate 30:232–42.

Zhou, J., R. E. Dutch, and R. A. Lamb. 1997. Spacing between heptad repeat B and the transmembrane domain boundary of the paramyxovirus SV5 F protein is critical for biological activity. Virology 239:327–339.

What is claimed is:

1. A recombinant nucleic acid segment comprising a simian virus 5 genome wherein the genome does not express a functional simian virus 5 membrane bound hemagglutinin-neuraminidase (HN) protein, and wherein the nucleic acid segment comprises the coding sequence for a fusion of the cytoplasmic and membrane spanning regions of a simian virus 5 membrane protein and a foreign extracellular cell targeting protein region.

2. An isolated nucleic acid molecule comprising the full length complement of the nucleic acid segment of claim 1.

3. The nucleic acid segment of claim 1, wherein the coding sequence for a fusion of the cytoplasmic and membrane spanning regions of a simian virus 5 protein and an extracellular cell targeting protein region is inserted into the simian virus 5 genome in the position of the hemagglutinin-neuraminidase (HN) protein coding sequence.

4. The nucleic acid segment of claim 3, wherein the extracellular cell targeting protein region is a single chain Fv antibody or a receptor ligand.

5. The nucleic acid segment of claim 4, wherein the single chain Fv antibody is immunoreactive with HER-2.

6. The nucleic acid segment of claim 4, wherein the single chain Fv antibody is immunoreactive with prostate specific membrane antigen.

7. The nucleic acid segment of claim 3, further defined as comprising one or more internal ribosome entry sites operably linked to a coding sequence for a polypeptide including a foreign protein domain or a cytotoxic agent.

8. The nucleic acid segment of claim 1, further comprising a coding sequence for a cytotoxic agent, wherein the cytotoxic agent is expressed from a gene start and gene end signal of simian virus 5.

9. The nucleic acid segment of claim 8, wherein the nucleic acid segment comprises an internal ribosome entry site operatively linked to the coding sequence for a cytotoxic agent.

10. The nucleic acid segment of claim 9, wherein the cytotoxic agent is a Pseudomonas exotoxin.

11. The nucleic acid segment of claim 9, wherein the cytotoxic agent is herpes simplex thymidine kinase.

12. The nucleic acid segment of claim 1, wherein the cytoplasmic and membrane spanning regions of a simian virus 5 membrane protein are encoded by a simian virus fusion (F), hemagglutinin-neuraminidase (HN), or small hydrophobic integral membrane (SH) gene segment.

13. The nucleic acid segment of claim 1, wherein the cytoplasmic and membrane spanning regions of a simian virus 5 membrane protein are encoded by a simian virus fusion (F) gene segment.

14. The composition of claim 1, wherein said genome is encapsulated in a lipid membrane.

15. A composition comprising a nucleic acid segment wherein the segment comprises a simian virus 5 genome and further wherein the genome contains a nucleic acid sequence that encodes a membrane bound protein having an extracellular region, and wherein the extracellular region binds to a target molecule other than sialic acid.

16. The composition of claim 15, wherein said genome is encapsulated in a lipid membrane and wherein the viral vector does not express an integral membrane bound hemagglutinin-neuraminidase (HN) protein on the surface of the lipid membrane due to a mutation in the hemagglutinin-neuraminidase (HN) gene region of said simian virus 5 genome.

17. The composition of claim 16, wherein the mutation in the hemagglutinin-neuraminidase (HN) gene region is a deletion of at least a portion of the hemagglutinin-neuraminidase (HN) gene coding region.

18. The composition of claim 17, wherein the deletion is between the simian virus 5 hemagglutinin-neuraminidase (HN) gene start and gene end sequences.

19. The composition of claim 17, wherein the deletion is from a NaeI restriction site at the 5' end of the hemagglutinin-neuraminidase (HN) gene region to a NdeI restriction site at the 3' end of the HN gene region.

20. The composition of claim 16, wherein the membrane bound protein comprises the cytoplasmic and membrane spanning regions of simian virus 5 fusion (F) protein, hemagglutinin-neuraminidase (HN) protein, or small hydrophobic integral membrane (SH) protein.

21. The composition of claim 16, wherein the membrane bound protein comprises the cytoplasmic and membrane spanning regions of simian virus 5 fusion (F) protein.

22. The composition of claim 21, wherein the membrane bound protein comprises a portion of the extracellular region of simian virus 5 fusion (F) protein.

23. The composition of claim 16, wherein the membrane bound protein comprises the amino acids encoded by bases 1443 to 1616 of simian virus 5 fusion (F) protein.

24. The composition of claim 16, wherein the membrane bound protein comprises from one to about 38 amino acids encoded by bases 1329 to 1442 of the extracellular region of simian virus 5 fusion (F) protein, and wherein said amino acids are in the order in which they occur in the native protein.

25. The composition of claim 15, wherein the extracelluar portion comprises a single chain antibody domain.

26. The composition of claim 25, wherein the antibody domain is immunoreactive with a tumor cell surface associated antigen.

27. The composition of claim 26, wherein the tumor cell surface associated antigen is HER2.

28. The composition of claim 26, wherein the tumor cell surface associated antigen is prostate specific membrane antigen.

29. The composition of claim 15, wherein the target molecule is a growth factor receptor.

30. The composition of claim 15, wherein the extracellular portion is a receptor ligand.

31. The composition of claim 30, wherein the receptor ligand is an epidermal growth factor receptor ligand.

32. The composition of claim 15, wherein the composition comprises a pharmaceutically acceptable solution.

33. A nucleic acid segment made by the method of:

(a) obtaining a plasmid containing a DNA copy of a simian virus 5 genome;

(b) deleting a portion of the hemagglutinin-neuraminidase (HN) gene region from the DNA copy of the simian virus 5 genome to obtain an HN deletion;

(c) inserting into the HN deletion, a nucleic acid segment including a coding sequence for a fusion of a simian virus 5 membrane protein cytoplasmic and membrane spanning regions fused to an extracellular targeting region, wherein the extracellular region binds to a target molecule other than sialic acid;

(d) transferring the plasmid into a cell;

(e) transferring helper plasmids that express viral replication proteins, nucleocapsid protein (NP), phosphoprotein (P) and polymerase protein (L) into the cell;

(f) generating the correct 3' end of the DNA; and (g) recovering the nucleic acid segment from the cell.

34. The nucleic acid segment of claim 33, wherein the cell targeting region is a single chain Fv antibody or a receptor ligand.

35. The nucleic acid segment of claim 33, wherein the simian virus 5 membrane protein cytoplasmic and membrane spanning regions are derived from simian virus 5 fusion (F) protein, hemagglutinin-neuraminidase (HN) protein or small hydrophobic integral membrane (SH) protein.

36. The nucleic acid segment of claim 33, wherein the simian virus 5 membrane protein cytoplasmic and membrane spanning regions are derived from simian virus 5 fusion (F) protein.

37. The nucleic acid segment of claim 33, wherein the method further comprises inserting into the genome a nucleic acid segment encoding a cytotoxic agent and simian virus 5 gene start and end sequences effective to express the cytotoxic agent in a cell.

38. The nucleic acid segment of claim 33, wherein the cell expresses a T7 RNA polymerase and the NP, P and L proteins are expressed from T7 RNA polymerase promoters.

* * * * *